(12) United States Patent
Strahl et al.

(10) Patent No.: US 9,278,209 B2
(45) Date of Patent: Mar. 8, 2016

(54) COCHLEAR IMPLANT ELECTRODE WITH LIQUID METAL ALLOY

(71) Applicant: MED-EL Elektromedizinische Geraete GmbH, Innsbruck (AT)

(72) Inventors: Stefan Strahl, Innsbruck (AT); Anandhan Dhanasingh, Innsbruck (AT); Claude Jolly, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/479,471

(22) Filed: Sep. 8, 2014

(65) Prior Publication Data

US 2015/0073520 A1   Mar. 12, 2015

Related U.S. Application Data

(60) Provisional application No. 61/874,388, filed on Sep. 6, 2013.

(51) Int. Cl.
*A61N 1/05* (2006.01)

(52) U.S. Cl.
CPC .................................. *A61N 1/0541* (2013.01)

(58) Field of Classification Search
None
See application file for complete search history.

(56) References Cited

U.S. PATENT DOCUMENTS

| | | | |
|---|---|---|---|
| 2003/0098170 A1 | 5/2003 | Easter | |
| 2004/0236390 A1* | 11/2004 | Dadd et al. | 607/55 |
| 2006/0193569 A1* | 8/2006 | Huston et al. | 385/100 |
| 2006/0200048 A1* | 9/2006 | Furst et al. | 600/585 |
| 2008/0077216 A1 | 3/2008 | Chitre et al. | |
| 2009/0171336 A1 | 7/2009 | Weber | |
| 2010/0272299 A1 | 10/2010 | Van Schuylenbergh et al. | |
| 2010/0312294 A1 | 12/2010 | Martinez et al. | |
| 2011/0125222 A1 | 5/2011 | Perkins et al. | |
| 2011/0178587 A1* | 7/2011 | Chambers | 607/137 |
| 2013/0006339 A1 | 1/2013 | March et al. | |

OTHER PUBLICATIONS

International Searching Authority, Authorized Officer Blaine R. Copenheaver, International Search Report and Written Opinion—PCT/US2014/054470, date of mailing Dec. 22, 2014, 13 pages.

* cited by examiner

*Primary Examiner* — Erica Lee
(74) *Attorney, Agent, or Firm* — Sunstein Kann Murphy & Timbers LLP

(57) ABSTRACT

A cochlear implant electrode includes an implantable array carrier made of flexible material with electrode contacts distributed on its outer surface along a longitudinal axis. Electrode wires are embedded within the array carrier, each electrode wire having a terminal end electrically connected to a corresponding electrode contact for applying electrical stimulation signals carried by the electrode wires to adjacent neural tissue within the cochlea. Each electrode wire has an inner non-crystal conductive material surrounded by a flexible outer seal. The flexible material of the array carrier is configured to be reactive with the non-crystal conductive material of the electrode wires so that if a break occurs in the outer seal of an electrode wire that allows contact between the flexible material and the non-crystal conductive material, then a local leakage seal will form at the break that resists migration of the non-crystal conductive material to the outer surface of the array carrier.

11 Claims, 4 Drawing Sheets

COCHLEAR IMPLANT ELECTRODE WITH LIQUID METAL ALLOY

This application claims priority from U.S. Provisional Patent Application 61/874,388, filed Sep. 6, 2013, which is incorporated herein by reference.

FIELD OF THE INVENTION

The present invention relates to implantable electrodes for medical devices and specifically to mechanical fixation of a hydrogel covering over the electrode contacts.

BACKGROUND ART

A normal ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode.

FIG. 1 also shows some components of a typical cochlear implant system where an external microphone provides an audio signal input to an external signal processor 111 in which various signal processing schemes can be implemented. The processed signal is then converted into a digital data format for transmission by external transmitter coil 107 into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrode contacts 112 on its surface that provide selective stimulation of the cochlea 104.

After an electrode array has been implanted, the body can react by forming fibrous tissue around the array. This adversely affects the impedance and charge transfer from the electrode contacts, and thus should be avoided or minimized One way to do that is to form a layer of hydrogel material over the electrode contacts. Such hydrogel material is biocompatible and electrically conductive so as to allow for the intended charge transfer from the electrode contact to the adjacent tissue. But the hydrogel material also prevents the direct contact of the metal material of the electrode contacts (e.g., platinum) with the cochlear tissue and thereby avoids formation of the undesirable fibrous tissues over the electrode contacts. See, for example, U.S. Pat. Nos. 5,786,439, 7,519,435, 7,519,435, 8,190,271; which are incorporated herein by reference.

The hydrogel materials swells when it contacts the perilymph fluid within the cochlea, absorbing more than its own dry weight. As this swelling occurs, polymer branches in the hydrogel matrix grow much larger, forcing the hydrogel material away from the electrode surface it lies against. The chemical bond that normally is used to connect the hydrogel material to the electrode array often is not strong enough to resist these swelling induced forces. When that happens, the hydrogel material separates from the electrode array and can undesirably wander away from the implanted array. One solution to this is described in the priority application, U.S. Provisional Patent Application 61/874,388, filed Sep. 6, 2013, which is incorporated herein by reference in its entirety.

Cochlear implants system exhibit high overall reliability. One cause of the rare failures in such systems is the occurrence of open circuits within the electrode array. See Carlson et al., *Prevalence and Timing of Individual Cochlear Implant Electrode Failures*, Otol Neurotol. 2010 Aug. 31 (6):893-8; which is incorporated herein by reference in its entirety. The main cause of open circuits within cochlear electrode arrays is externally applied force to the metal wires within the silicone array carrier. These forces can occur momentarily with a high amplitude due to an accident, or they may occur chronically at lower amplitude due to micro-movements induced by muscular activity. These forces applied to the metal structure of the electrode wires results in material fatigue and ultimately a mechanical failure, i.e. wire breakage.

To divert/distribute externally applied forces, the electrode wires can be wave-shaped so that induced force moves the entire flexible electrode array and only a fraction of the external force energy directly affects the metal structure of the electrode wire. See U.S. Pat. No. 8,112,161, which is incorporated herein by reference in its entirety. It also is known to achieving a certain stretch-ability by means of defined microstructures such as by thin-film technique, ribbons or grapheme. See, e.g., Someya, Takao (Editor), *Stretchable Electronics*, Wiley, 484 pages, December 2012, ISBN: 978-3-527-32978-6; which is incorporated herein by reference in its entirety. Some cochlear implant systems also implement multiple redundant electrode contacts and/or electrode wires within the electrode array to allow for the deactivation of an affected electrode(s) without a loss of clinical benefit of the cochlear implant. But if the loss of the clinical benefit is too large, then a revision surgery can be performed, to replace the defective part.

Sometimes, cochlear implant electrodes can contain drugs or chemicals. To avoid ototoxic reactions (i.e. damage to the inner ear due to unintended exposure of drugs or chemicals), the electrode wires are encased in a silicone array carrier and the electrode contacts are made of platinum. See, e.g., Stöver et al., *Biomaterials in Cochlear Implants*, GMS Curr Top Otorhinolaryngol Head Neck Surg. 2009; 8: Doc10; which is incorporated herein by reference in its entirety.

An alternative approach is taught in U.S. Patent Publication 20130006339 and U.S. Patent Publication 20090171336, which disclose metal wires comprising liquid metal instead of solid metal. But, these publications do not address problems that can arise when such liquid metal wires break.

SUMMARY OF THE INVENTION

Embodiments of the present invention are directed to a cochlear implant electrode that includes an implantable array carrier made of flexible material with electrode contacts distributed on its outer surface along a longitudinal axis. Electrode wires are embedded within the array carrier, each electrode wire having a terminal end electrically connected to a corresponding electrode contact for applying electrical stimulation signals carried by the electrode wires to adjacent neural tissue within the cochlea. Each electrode wire has an inner non-crystal conductive material surrounded by a flexible outer seal. A flexible material of the array carrier is configured to be reactive with the non-crystal conductive material of the electrode wires so that if a break occurs in the outer seal of an electrode wire that allows contact between the flexible material and the non-crystal conductive material, then a local leakage seal will form at the break that resists migration of the non-crystal conductive material to the outer surface of the array carrier.

The non-crystal conductive material may specifically be a liquid metal alloy material such as eutectic gallium indium material. In that case, the flexible material of the array carrier can be oxygen donor chelates such as hydroxypyridinone, or terephthalamide. The outer seal of the electrode wires may specifically be made of styrene ethylene butylene styrene block copolymer (SEBS) material. There may be an array cover made of non-toxic and/or biocompatible material around the array carrier that establishes an additional leakage barrier to further resist migration of the non-crystal conductive material if a break occurs in the outer seal of an electrode wire.

Each electrode contact may be a conductive metal surface embedded in an opening in the outer seal at the terminal end of an electrode wire. In addition or alternatively, there may be contact connectors made of conductive metal having a contact end connected to an electrode contact and a wire end connected to an electrode wire. There also may be contact covers made of hydrogel material that are mechanically connected to the outer surface of the array carrier over a corresponding electrode contact so as to form a contact leakage seal that resists migration of the non-crystal conductive material if a break occurs at the terminal end of a corresponding electrode wire.

DETAILED DESCRIPTION OF SPECIFIC EMBODIMENTS

Embodiments of the present invention are directed to a cochlear implant electrode that replaces conventional electrode wires that have a solid crystal structure such as platinum or platinum-iridium alloy, with electrode wires made of a sealed non-crystal conductive material such as a liquid metal alloy. External forces to the implant electrode then can be directly absorbed by the electrode wires via deformation that is at least partially reversible without any mechanical fatigue of the wire structure, i.e. without any lasting structural damage.

Figure 1:
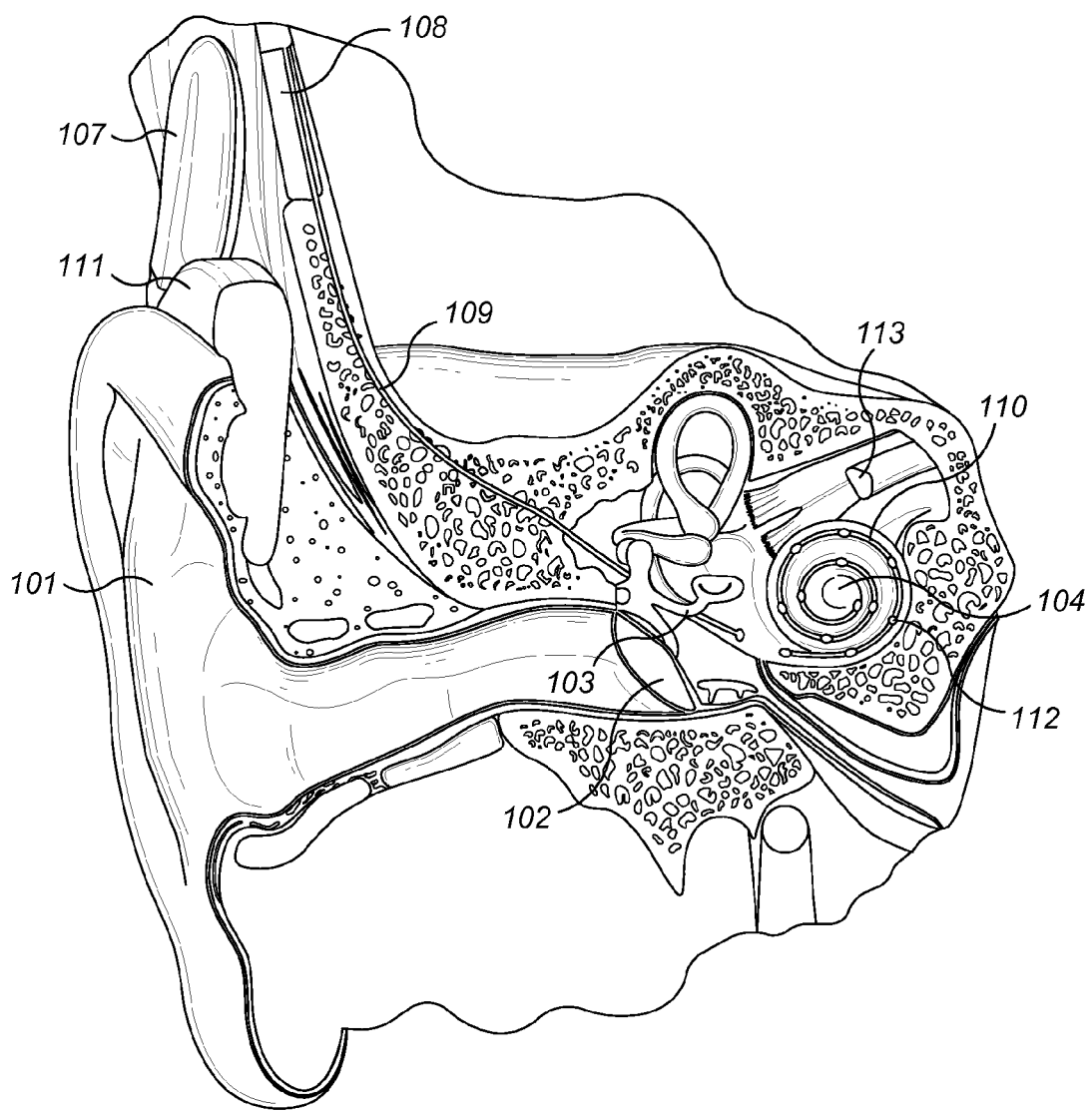
FIG. 1 shows the anatomy of the human ear with a cochlear implant system.
Figure 2:
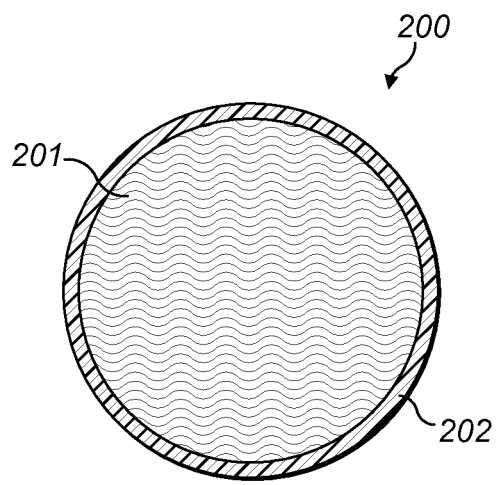
FIG. 2 shows a cross-sectional view of an electrode wire using a liquid metal alloy according to an embodiment of the present invention.

FIG. 2 shows a cross-sectional view of an electrode wire 200 using a liquid metal alloy according to an embodiment of the present invention. Each electrode wire 200 has an inner non-crystal conductive material 201 surrounded by a flexible outer seal 202. The non-crystal conductive material 201 may specifically be a liquid metal alloy material such as eutectic gallium indium material such as described in U.S. Pat. No. 5,508,003, which is incorporated herein by reference in its entirety. The outer seal 202 may specifically be made of styrene ethylene butylene styrene block copolymer (SEBS) material such as described by Zhu et al., *Ultrastretchable Fibers with Metallic Conductivity Using a Liquid Metal Alloy Core*, Adv. Funct. Mater. 2012 December, which is incorporated herein by reference in its entirety.

Figure 3:
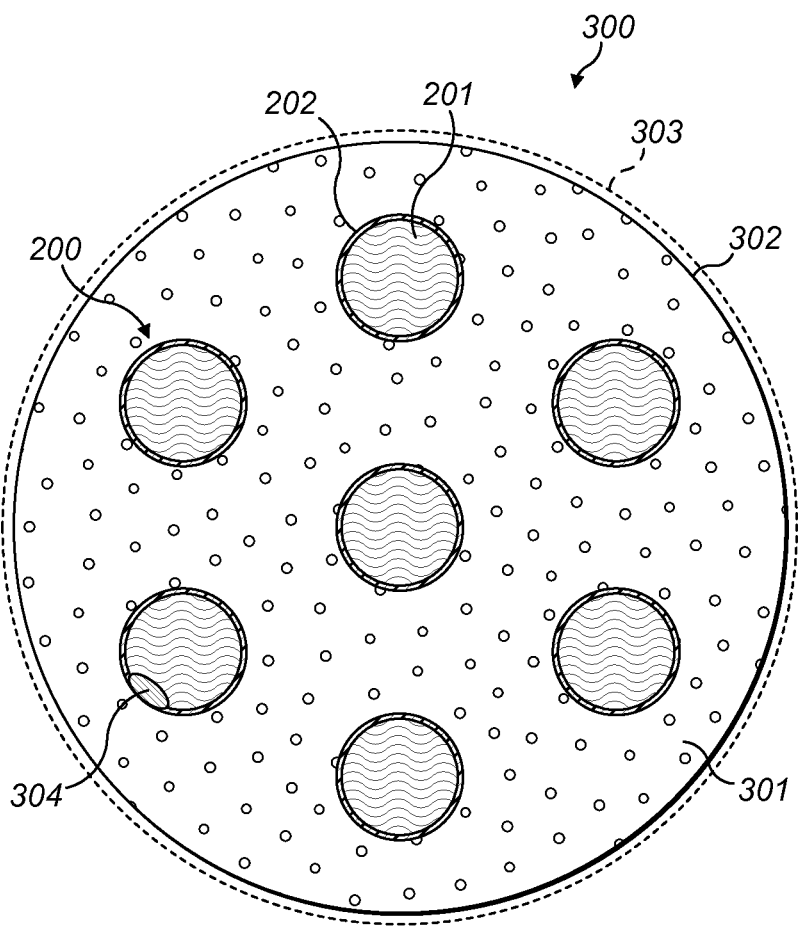
FIG. 3 shows a cross-sectional view of an electrode array carrier with multiple electrode wires according to an embodiment of the present invention.

For application in a medical product such as a cochlear implant electrode, the liquid metal alloy of the inner non-crystal conductive material 201 needs to be secured against leaking into the adjacent tissue in case of damage to the outer seal 202. This can be achieved by embedding the electrode wires 200 within a protective layer of a non-toxic material. FIG. 3 shows a specific example where multiple electrode wires 200 are embedded in an implantable array carrier 300.

The array carrier 300 is made of a flexible material 301 that is configured to be reactive with the non-crystal conductive material 201 of the electrode wires 200 so that if a break occurs in the outer seal 202 of an electrode wire 200 that allows contact between the carrier material 301 and the non-crystal conductive material 201, then a local leakage seal 304 will form at the break (like a coagulation scab around a wound on the skin) that resists migration of the non-crystal conductive material 201 to the outer surface 302 of the array carrier 300. Although this local leakage seal 304 may itself be rather stiff and inflexible, the electrode array as whole will remain very flexible because the local leakage seal 304 is formed only in a very limited volume at the site of the break.

For example, where the non-crystal conductive material 201 is eutectic gallium indium material, the carrier material 301 may include oxygen donor chelates such as hydroxypyridinone, or terephthalamide which are known to form biocompatible macromolecular dendrimer conjugates. See, e.g. Klemm et al., *Conjugation to Biocompatible Dendrimers Increases Lanthanide T2 Relaxivity of Hydroxypyridinone (HOPO) Complexes for Magnetic Resonance Imaging (MRI)*, Eur J Inorg Chem. April 2012; 2012(12): 2108-2114, which is incorporated herein by reference in its entirety. When a break occurs in the outer seal 202 of an electrode wire 200, the leaking eutectic gallium indium material of the inner conductive material 201 would then interact with passive oxygen donors of the chelating agents embedded in the carrier material 301 to form a local leakage seal 304 made of non-flexible gallium oxide in the form of macromolecular dendrimers. In other embodiments, the carrier material might be a conventional silicone carrier material with enough passive oxygen donors to interact with any leaking conductive material 201 so as to form a local leakage seal 304.

In some embodiments, there may be an array cover 303 around the outer surface 302 of the electrode carrier 300 that establishes an additional leakage barrier to further resist migration of the non-crystal conductive material 201 if a break occurs in the outer seal 202 of an electrode wire 200. For example, the array cover 303 may be made of a polymer based flexible mesh. In case there was any leakage that reached the outer surface 302 of the electrode carrier 300, the mesh of the array cover 303 would resist any leakage material from reaching the adjacent tissues and fluids.

Figure 4:
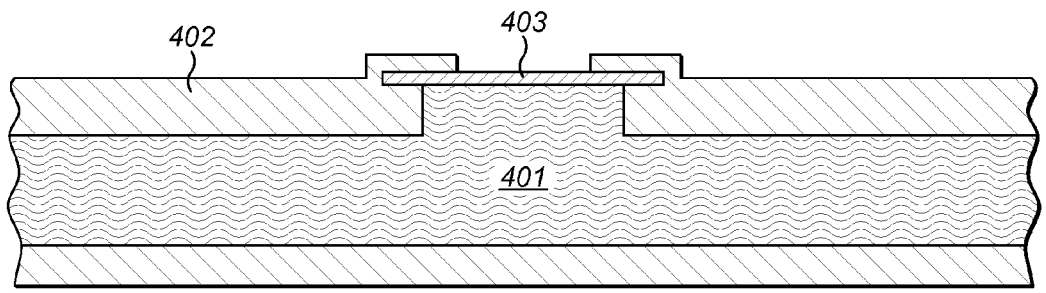
FIG. 4 shows a detail of a side cross-section of an electrode array at an electrode contact according to an embodiment of the present invention.

It is important that the electrical and mechanical connection between the liquid conductive material and the electrode contacts be secure against leakage in the event of a break at that point. FIG. 4 shows a detail of a side cross-section of an electrode array at an electrode contact 403 that is a conductive metal surface embedded in an opening in the outer seal 402 that is in contact on its surface with the inner conductive material 401.

Figure 5:
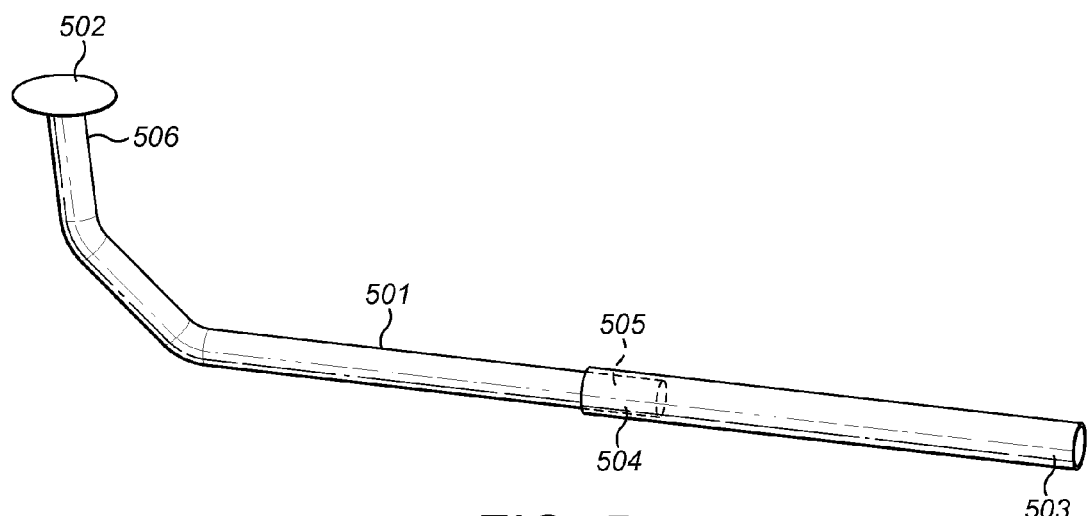
FIG. 5 shows an elevated perspective view of an electrode wire connected to an electrode contact by a metal tube contact connector according to an embodiment of the present invention.

FIG. 5 shows an elevated perspective view of an electrode wire 503 connected to an electrode contact 502 by a metal tube contact connector 501. The contact connector 501 is made of conductive metal which is welded or mechanically connected by other means at the contact end 506 to the electrode contact 502. The electrode wire 503 fits over the wire end of the contact connector 501 by a tube fitting end 504 that forms a leak proof connection. The length ratio between the contact connector 501 and the silicone based tube fitting end 504 can be chosen to either reduce stiffness (short contact connector 501, long tube fitting end 504) or increase the leak protection close to the outer surface of the electrode array (long contact connector 501, short tube fitting end 504).

But a break at the connection point between the contact connector 501 and the terminal end of the electrode wire 503 could cause leakage of the liquid metal alloy inner conductive material towards the boundary between the electrode contact 502 and its opening in the silicone array carrier. Since the electrode contact 502 needs electrical contact with the cochlear fluid to provide the electrical stimulation signal, any such leaking liquid metal alloy could get in contact with the cochlear fluids at the top side of the electrode contact 502.

Figure 6:
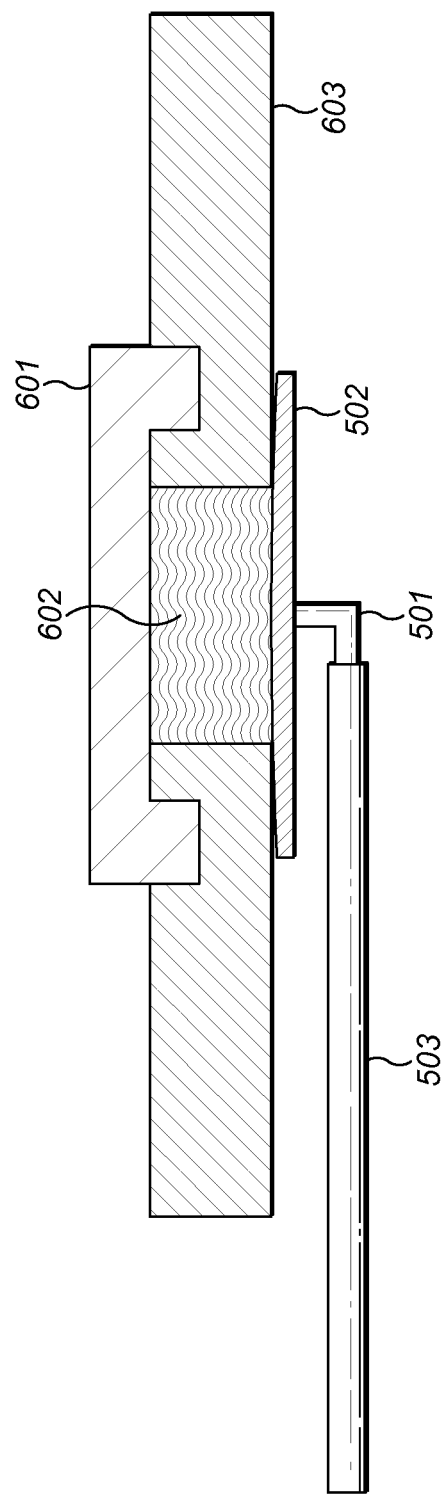
FIG. 6 shows a side cross-sectional view of an electrode contact covered by a hydrogel band according to an embodiment of the present invention.

To avoid that situation, the open contact surface of the electrode contacts may be covered by a hydrogel layer as described in the priority application, U.S. Provisional Patent Application 61/874,388. FIG. 6 shows a side cross-sectional view of an electrode contact 502 covered by a hydrogel contact cover 601 over the open contact surface that is mechanically connected to the outer surface of the array carrier 603 so as to form a contact leakage seal 602 that resists migration of the non-crystal conductive material if a break occurs at the terminal end of a corresponding electrode wire 503.

The idea of electrode wires implemented with a non-crystal conductive material such as a liquid metal alloy is of course not necessarily limited to the specific context of a cochlear implant. For example, such electrode wires could be useful in hearing implants that involve mechanical stimulation such as middle ear implants that use a floating mass transducer and/or bone conduction implants. In such applications, the mechanical stimulating transducer is completely encapsulated, for example, within an insulating tubing or some other structure with a connection to another tubular structure containing the liquid metal alloy conductor. Also other medical implants may find such electrode wires useful, for example, vestibular implants or laryngeal pacemaker implants.

Embodiments of the present invention such as those described herein remove an open circuit in the electrode array as a cause of failure for a cochlear implant. In addition, the electrode array is more flexible and its atraumaticity is increased. In most leakage scenarios, the flexible conductive material is contained within the electrode array, though of course, if the electrode carrier were severely damaged—for example if the electrode carrier is accidentally cut during surgery—the liquid metal alloy conductive material might escape into the exposed tissues with possible toxic effects.

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant electrode comprising:
   an implantable array carrier having a center longitudinal axis and an outer surface;
   a plurality of electrode contacts distributed on the outer surface of the array carrier along the longitudinal axis for applying electrical stimulation signals to adjacent neural tissue; and
   a plurality of electrode wires embedded within the array carrier for conducting electrical stimulation signals, each electrode wire having a terminal end electrically connected to a corresponding electrode contact;
   wherein each electrode wire comprises an inner liquid conductive material surrounded by an outer seal; and
   wherein the array carrier is configured to react with the liquid conductive material of the electrode wires when contact occurs between the array carrier and the liquid conductive material to form a local leakage seal configured to resist migration of the liquid conductive material to the outer surface of the array carrier.

2. The electrode according to claim 1, wherein the liquid conductive material is a liquid metal alloy material.

3. The electrode according to claim 2, wherein the liquid metal alloy material is eutectic gallium indium material.

4. The electrode according to claim 3, wherein the array carrier is formed from an oxygen donor chelate material.

5. The electrode according to claim 4, wherein the oxygen donor chelate material is hydroxypyridinone, or terephthalamide.

6. The electrode according to claim 1, wherein the outer seal of the electrode wires is made of styrene ethylene butylene styrene block copolymer (SEBS) material.

7. The electrode according to claim 1, further comprising:
   an array cover, around the array carrier, configured to further resist migration of the liquid conductive material to the outer surface of the array carrier.

8. The electrode according to claim 1, wherein each electrode contact is a conductive metal surface embedded in an opening in the outer seal at the terminal end of an electrode wire.

9. The electrode according to claim 1, further comprising:
   a plurality of contact connectors made of conductive metal, each contact connector having a contact end connected to an electrode contact and a wire end connected to the electrode wire.

10. The electrode according to claim 9, further comprising:
    a plurality of contact covers made of hydrogel material, each contact cover being mechanically connected to the outer surface of the array carrier over a corresponding electrode contact so as to form a contact leakage seal that resists migration of the liquid conductive material if a break occurs at the terminal end of a corresponding electrode wire.

11. A cochlear implant with an electrode according to any of the preceding claims.

* * * * *